United States Patent [19]
Nishitani et al.

[11] Patent Number: 4,795,814
[45] Date of Patent: Jan. 3, 1989

[54] PROCESS FOR PREPARING NOVEL DIHYDROPYRIDINE DERIVATIVES

[75] Inventors: Shinji Nishitani, Tokushima; Junichi Minamikawa, Naruto, both of Japan; Masanobu Kano, Gainesville, Fla.; Junichiro Otsubo; Yoshiaki Manabe, both of Tokushima,, Japan

[73] Assignee: Otsuka Pharmaceutical Co., Ltd., Tokyo, Japan

[21] Appl. No.: 942,915

[22] Filed: Dec. 18, 1986

Related U.S. Application Data

[63] Continuation of Ser. No. 761,702, Aug. 2, 1985, abandoned.

[30] Foreign Application Priority Data

Aug. 7, 1984 [JP] Japan ................................. 59-165797

[51] Int. Cl.$^4$ ........................................... C07D 211/02
[52] U.S. Cl. ..................... 546/249; 546/321; 546/269
[58] Field of Search ................................ 546/321, 249

[56] References Cited

U.S. PATENT DOCUMENTS 4,031,104 6/1977 Bossert et al. ...................... 546/321
4,044,141 8/1977 Bossert et al. ...................... 546/321

OTHER PUBLICATIONS

Jones, G., "The Knoevenagel Condensation", *Organic Reactions*, vol. 15, John Wiley & Sons, NY (1967).

Primary Examiner—Jane T. Fan
Attorney, Agent, or Firm—Finnegan, Henderson, Farabow, Garrett & Dunner

[57] ABSTRACT

Process for preparing dihydropyridine derivatives and salts and esters thereof represented by the general formula

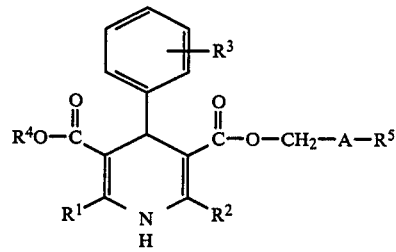

from a phenyl derivative and an enamine derivative in which the phenyl derivative is prepared by reacting a compound of the formula

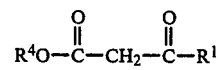

with a compound of the formula

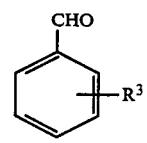

in the presence of an aromatic amine selected from o-, m-, p- anisidine; m-, p-toluidine; p-chloroaniline; aniline and o-phenetidine.

2 Claims, No Drawings

PROCESS FOR PREPARING NOVEL DIHYDROPYRIDINE DERIVATIVES

This is a continuation of application Ser. No. 761,702 filed Aug. 2, 1985 now abandoned.

FIELD OF THE INVENTION

The present invention relates to process for preparing novel dihydropyridine derivatives. More particularly, the present invention relates to process for preparing novel dihydropyridine derivatives and salts thereof represented by the general formula (1),

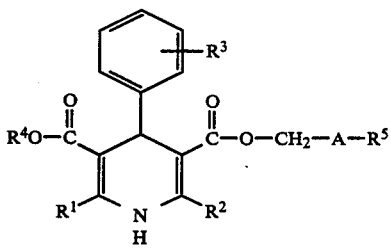

(1)

[wherein $R^1$, $R^2$ and $R^4$ are each a lower alkyl group; $R^3$ is a nitro group or a lower alkyl group which may have 1 to 3 halogen atoms as the substituents; $R^5$ is a phenyl group which may have 1 to 3 substituents selected from the group consisting of a lower alkoxy group, a halogen atom, a lower alkylthio group, a hydroxyl group, a lower aklanoyloxy group, a tetrahydropyranyloxy group and a lower alkoxylower alkoxy group; and A is an unsaturated straight- or branched-chain hydrocarbon residue].

Dihydropyridine derivatives and salts thereof represented by the general formula (1) are novel compounds and they possess excellent calcium antagonist effect, hypotensive effect, platelets aggregation inhibitory effect, phosphodiesterase inhhibitory effect, calmodulin inhibitory effect and peroxidized lipid lowering effect, thus they are useful as coronary blood flow improving agents such as coronary vasodilator, hypotensive agent, prophylaxis and treating agents for thrombosis, phosphodiesterase inhibitory agents, peroxidized lipid metabolism lowering agents, anti-inflammatory agents as well as anti-tumorigenic agents.

DESCRIPTION OF THE PRIOR ART

Compounds similar to the dihydropyridine derivatives and salts thereof represented by the general formula (1) are known from some prior art literatures, for example, Japanese Patent Pre-examination Application No. 51-108075 (1976) and 56-36455 (1981). Compounds disclosed in these prior art literatures are known as useful hypotensive agents, peripheral and cerebral vasodilating agents and treating agents for coronary blood vessels. On the contrary, dihydropyridine derivatives and salts thereof represented by the general formula (1) have features in that they perform the above-mentioned pharmacological effects for longer period of time with less side-effects as compared with known compounds.

SUMMARY OF THE INVENTION

An object of the present invention is to provide process for preparing novel dihydropyridine derivatives and salts thereof.

Further objects and features of the present invention will become apparent from the following description.

DETAILED DESCRIPTION OF PREFERRED EMBODIMENTS

Dihydropyridine derivatives and salts thereof represented by the general formula (1), examples of various substituents as defined in $R^1$, $R^2$, $R^3$, $R^4$, $R^5$ and A are as follows.

As to the lower alkyl group, an alkyl group having 1 to 6 carbon atoms, such as methyl, ethyl, propyl, isopropyl, butyl, tert-butyl, pentyl and hexyl groups can be exemplified.

As to the lower alkyl group which may have 1 to 3 halogen atoms as the substituents, an alkyl group having 1 to 6 carbon atoms which may have 1 to 3 halogen atoms as the substituents, suc as in addition to the above-mentioned alkyl groups having 1 to 6 carbon atoms, trifluoromethyl, 2,2-difluoroethyl, 1,1-dichloroethyl, troichloromethyl, dichloromethyl, tribromomethyl, 2,2,2-trifluoroethyl, 2,2,2-trichloroethyl, 2-chloroethyl, 1,2-dichloroethyl, 3,3,3-trichloropropyl, 3-fluoropropyl, 4-chlorobutyl and 3-chloro-2-methylethyl groups can be exemplified.

As to the lower alkoxy group, an alkoxy group having 1 to 6 carbon atoms such as methoxy, ethoxy, propoxy isopropoxy, butoxy, tert-butoxy, pentyloxy and hexyloxy groups can be exemplified.

As to the halogen atoms, fluorine atom, chlorine atom, bromine atom and iodine atom can be exemplified.

As to the lower alkoxy-lower alkoxy group, an alkoxyalkoxy groups in which each of the alkoxy moieties having 1 to 6 carbon atoms, such as methoxymethoxy, 2-methoxyethoxy, 1-methoxyethoxy, 3-methoxypropoxy, 4-methoxybutoxy, 1,1-dimethyl-2-methoxyethoxy, 5-methoxypentyloxy, 6-methoxyhexyloxy, 2-methyl-3-methoxypropoxy, ethoxymethoxy, 3-ethoxypropoxy, 6-ethoxyhexyloxy, 2-propoxyethoxy, 4-propoxybutoxy, 5-butoxypentyloxy, pentyloxymethoxy, 1-pentyloxyethoxy, 1,1-dimethyl-2-hexyloxyethoxy and 3-hexyloxypropoxy groups can be exemplified.

As to the straight- or branched-chain unsaturated hydrocarbon residual group, a straight- or branched-chain unsaturated hydrocarbon residual group having 2 to 6 carbon atoms, having 1 to 3 double bonds or/and triple bonds, such as vinylene, 1-propenylene, 1-methyl-1-propenylene, 2-methyl-1-propenylene, 2-propenylene, 2-butenylene, 1-butenylene, 3-butenylene, 2-pentenylene, 1-pentenylene, 3-pentenylene, 4-pentenylene, 1,3-butadienylene, 1,3-pentadienylene, 2-penten-4-ylene, 2-hexenylene, 1-hexenylene, 5-hexenylene, 3-hexenylene, 4-hexenylene, 3,3-dimethyl-1-propenylene, 2-ethyl-1-propenylene, ethynylene, 2-propynylene, 1-propynelene, 1,1-dimethyl-2-propynylene, 3,3-dimethyl-1-propynylene, 2-butynylene, 3-butynylene, 1-butynylene, 2-pentynylene, 1-pentynylene, 3-pentynylene, 4-pentynylene, 2-hexynylene, 1-hexynylene, 3-hexynylene, 4-hexynylene, 5-hexynylene, 1,3-hexadienylene, 1,4-hexadienylene and 1,3,5-hexatrienylene groups can be exemplified.

As to the lower alkylthio group, an alkylthio group having 1 to 6 carbon atoms, such as methylthio, ethylthio, propylthio, isopropylthio, buthylthio, tert-butylthio, pentylthio and hexylthio groups can be exemplified.

As to the lower alkanoyloxy group, an alkanoyloxy group having 1 to 6 carbon atoms, such as formyloxy, acetyloxy, propionyloxy, butyryloxy, isobutyryloxy, pentanoyloxy, tert-butyryloxy and hexanoyloxy groups can be exemplified.

As to the phenyl group which may have 1 to 3 substituents selected from the group consisting of a lower alkoxy group, a halogen atom, a lower alkylthio group, a hydroxyl group, a lower alkanoyloxy group, tetrahydropyranyloxy group and a lower alkoxy-lower alkoxy group, a phenyl group which may have 1 to 3 substituents selected from the group consisting of an alkoxy group having 1 to 6 carbon atoms, a halogen atom, an alkylthio group having 1 to 6 carbon atoms, a hydroxyl group, an alkanoyloxy group having 1 to 6 carbon atoms, a tetrahydropyranyloxy group and an alkoxyalkoxy group in which each of the alkoxy moietiy having 1 to 6 carbon atoms, such as phenyl, 2-, 3- or 4-chlorophenyl, 2-, 3- or 4-fluorophenyl, 2-, 3- or 4-bromophenyl, 2-, 3- or 4-iodophenyl, 3,5-dichlorophenyl, 2,6-dichlorophenyl, 3,4-dichlorophenyl, 3,4-difluorophenyl, 3,5-dibromophenyl, 2-, 3- or 4-methylthiophenyl, 2-, 3- or 4-ethylthiophenyl, 4-propylthiophenyl, 3-isopropylthiophenyl, 2-butylthiophenyl, 4-hexylthiophenyl, 3-pentylthiophenyl, 4-tert-tubylthiophenyl, 3,4-dimethylthiophenyl, 2,5-dimethylthiophenyl, 2-, 3- or 4-methoxyphenyl, 2-, 3- or 4-ethoxyphenyl, 3-propoxyphenyl, 4-isopropoxyphenyl, 3-butoxyphenyl, 2-pentyloxyphenyl, 4-tert-butoxyphenyl, 4-hexyloxyphenyl, 3,4-dimethoxyphenyl, 3,4-diethoxyphenyl, 2,5-dimethoxyphenyl, 2-, 3- or 4-(2-tetrahydropyranyloxy)phenyl, 2,4-(2-tetrahydropyranyloxy)-phenyl, 3-methylthio-4-chlorophenyl, 2-chloro-6-methylthiophenyl, 2-methoxy-3-hydroxyphenyl, 3,4,5-trimethoxyphenyl, 3,4,5-trimethylthiophenyl, 3,4,5-trichlorophenyl, 2-, 3- or 4-hydroxyphenyl, 3,4-dihydroxyphenyl, 2,6-dihydroxyphenyl, 3,4,5-trihydroxyphenyl, 2-, 3- or 4-acetyloxyphenyl, 4-propionyloxyphenyl, 3-isopropionyloxyphenyl, 2-butyryloxyphenyl, 4-hexanoyloxyphenyl, 3-pentanoyloxyphenyl, 3,4-diacetyloxyphenyl, 2,5-diacetyloxyphenyl, 3,4,5-tridiacetyloxy phenyl, 2-methoxymethoxyphenyl, 3-(2-methoxyethoxy)phenyl, 4-(1-methoxyethoxy)phenyl, 2-(3-methoxypropoxy)phenyl, 3-(4-methoxybutoxy)-phenyl, 4-(1,1-dimethyl-2-methoxyethoxy)phenyl, 2-(5-methoxypentyloxy)phenyl, 3-(6-methoxyhexyloxy)phenyl, 4-(2-methol-3-methoxypropoxy)phenyl, 2-(ethoxymethoxy)phenyl, 3-(3-ethoxypropoxy)phenyl, 4-(4-ethoxyhexyloxy)phenyl, 2-(2-propoxyethoxy)phenyl, 3-(4-propoxybutoxy)phenyl, 4-(5-butoxypentyloxy)phenyl, 2-(pentyloxymethoxy)phenyl, 3-(1-pentyloxyethoxy)phenyl, 4-(1,1-dimethyl-2-hexyloxyethoxy)phenyl and 2-(3-hexyloxypropoxy)phenyl groups can be exemplified.

According to the present invention, dihydropyridine derivatives and salts thereof represented by the general formula (1),

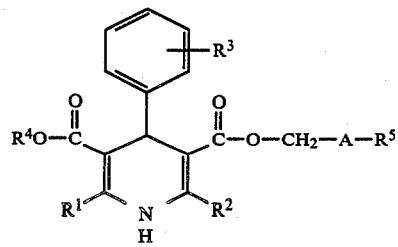

(1)

[wherein $R^1$, $R^2$, $R^3$, $R^4$, $R^5$ and A are the same as defined above] are prepared by reacting a phenyl derivative represented by the general formula (2),

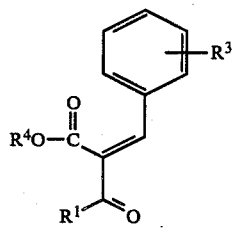

(2)

[wherein $R^1$, $R^3$ and $R^4$ are the same as defined above], with an enamine derivative represented by the general formula (3),

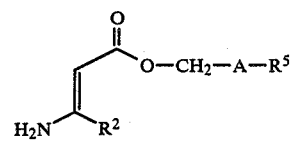

(3)

[wherein $R^2$, $R^5$ and A are the same as defined above].

According to the present invention, said dihydropyridine derivatives and salts thereof having high purity can be prepared by simple method in higher yield.

The reaction of a phenyl derivative represented by the general formula (2) with an enamine derivative represented by the general formula (3) is carried out in a suitable solvent in the presence of or absence of a basic compound. As to the solvent used in this reaction, any inert solvent which does not give any adverse effect can be used, such as ketones for example acetone and the like; halogenated hydrocarbons for example chloroform, dichloromethane, carbon tetrachloride and the like; alcohols for example methanol, ethanol, propanol, isopropanol, ethylene glycol and the like; ethers for example diethyl ether, tetrahydrofuran, dioxane, monoglyme, diglyme and the like; aromatic hydrocarbons for example benzene, toluene, xylene and the like; esters for example methyl acetate, ethyl acetate and the like; carboxylic acids for example acetic acid, propionic acid and the like; organic basic compounds for example pyridine and the like; aprotic polar solvents for example N,N-dimethylformamide, dimethyl sulfoxide, hexamethylphosphric triamide and the like can be exemplified.

The ratio of the amount of a compound of the general formula (2) to the amount of a compound of the general formula (3) may generally be at least an equimolar quantity, preferably an equimolar quantity to 1.5 times the molar quantities of the former may be used to the latter.

This reaction is carried out generally at −20° to 200° C., preferably at 50° to 150° C., and is completed in about 10 minutes to 20 hours.

As to the basic compound used in this reaction, organic basic compounds for example pyridine, piperidine, triethylamine, diethylamine, 1,8-diazabicyclo[5,4,0]undecene-7 (DBU) and the like; metallic alcoholates for example sodium ethylate, sodium methylate and the like; inorganic basic compounds for example sodium hydroxide, potassium hydroxide, potassium carbonate and the like can be exemplified. This reaction is advantageously carried out in the absence of basic compound.

A compound of the general formula (3) to be used as the starting material can be prepared by, for example the methods as shown in the following Reaction process formula-1 and -2.

Reaction process formula-1

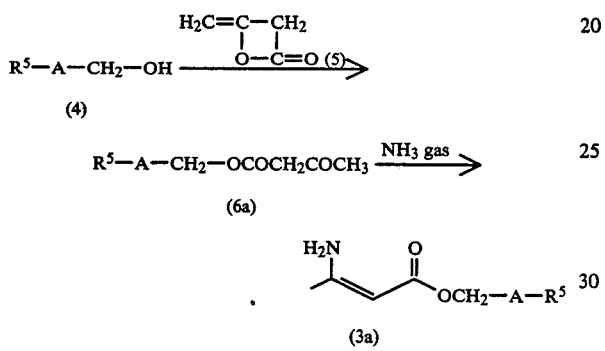

[wherein $R^5$ and A are the same as defined above].

In the above-mentioned Reaction process formula-1, the reaction of a compound (4) with ketene dimer (5) is carried out in a suitable solvent in the presence of a catalyst. As to the catalyst, basic compounds for example, organic basic compounds such as triethylamine, pyridine, N,N-dimethylaniline or the like; inorganic basic compounds such as sodium acetate, potassium carbonate and the like; acidic compounds for example, sulfonic acids such as p-toluenesulfonic acid and the like; Lewis acids such as boron trifluorid and the like can be exemplified. As to the solvent, aromatic hydrocarbons such as benzene, toluene, xylene and the like; esters such as methyl acetate, ethyl acetate and the like; halogenated hydrocarbons such as methylene chloride, chloroform, 1,2-dichloroethane and the like; ethers such as diethyl ether, tetrahydrofuran, dioxane, monoglyme, diglyme and the like; ketones such as acetone, methyl ethyl ketone and the like; aprotic polar solvents such as N,N-dimethylformamide, dimethyl sulfoxide, hexamethylphosphoric triamide, N-methylpyrrolidone and the like can be exemplified.

The ratio of the amount of a compound (4) to the amount of a compound (5) may generally be at least an equimolar quantity, preferably 1 to 2 times the molar quantities of the latter may be used to the former. The amount of the catalyst is not specifically restricted, and generally 1/100 to 10 times the molar quantities, preferably 1/10 to 5 times the molar quantities of catalyst may generally be used to a compound (4). The reaction is carried out generally at −20° to 200° C., preferably at −20° to 100° C., and is generally completed in about 10 minutes to 20 hours.

Next, the reaction of thus obtained compound (6) with ammonia gas may also be carried out in a suitable solvent. As to the solvent used in this reaction, aromatic hydrocarbons such as benzene, toluene, xylene and the like; alcohols such as methanol, ethanol, propanol, isopropanol, butanol, ethylene glycol and the like; ethers such as diethyl ether, tetrahydrofuran, monoglyme, diglyme and the like; halogenated hydrocarbons such as methylene chloride, chloroform, 1,2-dichloroethane and the like; aprotic polar solvents such as N,N-dimethylformamide, dimethyl sulfoxide, hexamethylphosphoric triamide and the like; carboxylic acids such as acetic acid, propionic acid and the like; and pyridine can be exemplified.

The amount of ammonia gas may be at least 1 chemical equivalent, generally 1 to 50 chemical equivalents may be used to a compound (6). The reaction is carried out, generally at −20° to 200° C., preferably at −20° to 150° C. and the eaction is completed generally in about 10 minutes to 10 hours.

Reaction process formula-2

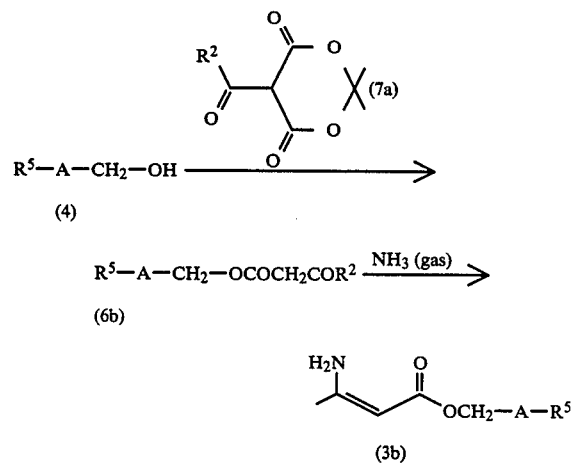

[wherein $R^2$, $R^4$, $R^5$ and A are the same as defined above].

The reaction of a compound (4) with a known compound (7a) can be carried out under conditions similar to those employed in the reaction of a compound (4) with a compound (5) in the above-mentioned Reaction process formula-1. Further, the reaction of a compound (6b) with ammonia gas can be carried under conditions similar to those employed in the reaction of a compound (6a) with ammonia gas in the above-mentioned Reaction process formula-1.

A compound of the general formula (2) used as the other starting material is prepared by a method, for example as shown in the following Reaction process formula-3.

Reaction process formula-3

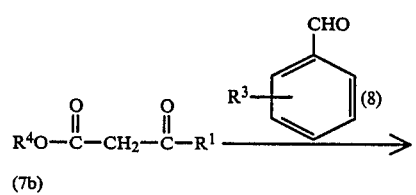

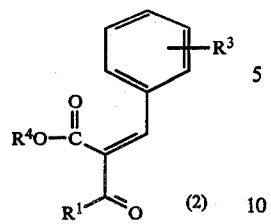

(2)

[wherein $R^1$, $R^3$ and $R^4$ are the same as defined above].

The reaction of a compound of the general formula (7b) with a compound of the general formula (8) is carried out in a suitable solvent in the presence of or absence of a catalyst. As to the solvent used in the reaction, alcohols such as methanol, ethanol, propanol, isopropanol, butanol, ethylene glycol and the like; ethers such as diethyl ether, tetrahydrofuran, dioxane, monoglyme, diglyme and the like; aromatic hydrocarbons such as benzene, toluene, xylene and the like; halogenated hydrocarbons such as methylene chloride, chloroform, 1,2-dichloroethane and the like; aprotic polar solvents such as N,N-dimethylformamide, dimethyl sulfoxide, hexamethylphosphoric triamide and the like; carboxylic acids such as acetic acid, propionic acid and the like can be exemplified. As to the catalyst used in the reaction, organic basic compounds such as piperidine, triethylamine, diethylamine, DBU and the like; aromatic amines such as pyridine, quinoline, isoquinoline, o-anisidine, p-anisidine, m-anisidine, m-toluidine, p-toluidine, p-chloroaniline, aniline, o-phenetidine and the like; metallic alcoholates such as sodium ethylate, sodium methylate and the like; inorganic basic compounds such as sodium hydroxide, potassium hydroxide, potassium carbonate, potassium acetate and the like; mineral acids such as hydrochloric acid, sulfurinc acid and the like; carboxylic acid such as acetic acid, propionic acid and the like; Lewis acids such as boron trifluoride and the like can be exemplified. Among those catalysts, aromatic amines are preferable catalysts.

The ratio of the amount of a compound (7b) to the amount of a compound (8) may generally be at least an equimolar quantity, preferably an equimolar quantity to 2 times the molar quantities of the latter is used to the former. As to the amount of the catalyst, there is not any specific restriction thereof, and generally, 1/100 to 10 times of the molar quantities, preferably 1/10 to 5 times the molar quantities of the catalyst may be used to a compound (7b).

This reaction is carried out, generally at −20° to 200° C., preferably at −20° to 150° C., and generally, the reaction is completed in about 10 minutes to 50 hours.

A compound of the general formula (4) used in the above-mentioned Reaction process formula-3 includees novel compounds, and such compounds the general formulas (4a), (4b), (4c), (4d) and (4f) can be prepared by the following Reaction process formula-4 to -8.

Reaction process formula-4

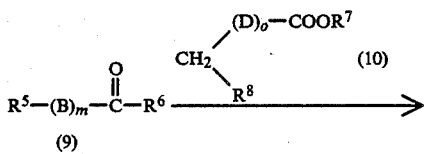

(9)

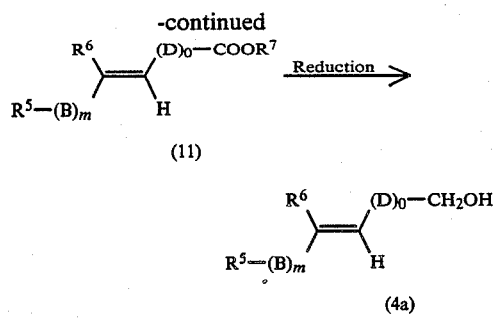

(11)

(4a)

[wherein $R^5$ is the same as defined above; $R^6$ is a hydrogen atom or a lower alkyl group; $R^7$ is a lower alkyl group, $R^8$ is a carboxyl group or a group of the formula $$-\underset{\underset{O}{\|}}{P}(OR^9)_2$$

(wherein $R^9$ is a lower alkyl group); B and D are unsaturated alkylene groups; m and o are each 0 or 1].

The reaction of a compound of the general formula (9) with a compound of the general formula (10) is carried out in the presence of a basic compound, in a suitable solvent. As to the basic compound used in this reaction, inorganic basic substances such as sodium metal, potassium metal, sodium hydride, sodium amide, sodium hydroxide, potassium hydroxide, sodium carbonate, potassium carnobate, sodium hydrogen carbonate and the like; metallic alcoholates such as sodium methylate, sodium ethylate and the like; organic basic compounds such as pyridine, piperidine, quinoline, triethylamine, N,N-dimethylaniline and the like can be exemplified. As to the solvent, any solvent which does not give any adverse effect may be used, for example ethers such as diethyl ether, dioxane, tetrahydrofuran, monoglyme, diglyme, and others; aromatic hydrocarbons such as benzene, toluene, xylene and the like; aliphatic hydrocarbons such as n-hexane, heptane, cyclohexane and the like; amines such as pyridine, N,N-dimethylaniline and the like; aprotic polar solvents such as N,N-dimethylformamide, dimethyl sulfoxide, hexamethylphosphoric triamide and the like can be exemplified.

The reaction temperature may generally be 0° to 150° C., preferably room temperature to about 120° C., and the reaction is generally completed 0.5 to about 15 hours.

The ratio of the amount of a compound of the general formula (10) to a compound of the general formula (9) may be at least an equimolar quantity, preferably an equimolar quantity to 2 times the molar quantities of the former to the latter.

The reduction of a compound of the general formula (11) may be carried out by using hydrogenating-reducing agent. As to the hydrogenating-reducing agent, sodium borohydride, lithium aluminum hydride, dialkylaluminum hydride such as diisobutylaluminum hydride (DIBAL) and the like and diborane may be exemplified. The ratio of the amount of said hydrogenating-reducing agent to the amount of a compound of the general formula (11) may generally be 0.1 to 3 times the molar quantities, preferably 0.5 to 2 times the molar quantities of the former to the latter.

This reduction is generally carried out in a suitable solvent, for example, water, lower alcohols such as methanol, ethanol, isopropanol and the like; ethers such as tetrahydrofuran, diethyl ether, diglyme and the like; aromatic hydrocarbons such as benzene, toluene, xylene and the like, and generally the reduction is carried out at −60° to 50° C., preferably at −40° C. to room temperature for about 10 minutes to 5 hours. Further, when lithium aluminum hydride, dialkylaluminum hydride or diborane is used as the reducing agent, anhydrous solvent such as diethyl ether, tetrahydrofuran, diglyme, benzene, toluene, xylene or the like may advantageously be used.

Reaction process formula-5

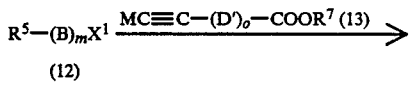

(12)

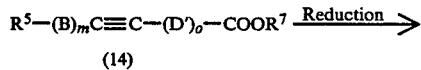

(14)

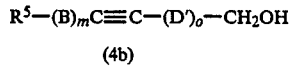

(4b)

[wherein $R^5$, $R^7$, B, m and o are the same as defined above; $X^1$ is a halogen atom; M is a metal such as copper sodium, lithium, or potassium; D' is a saturated or unsaturated alkylene group].

The reaction of a compound of the general formula (12) with a compound of the general formula (13) is carried out in a suitable solvent. As to the solvent used in this reaction, ethers such as diethyl ether, dioxane, tetrahydrofuran, monoglyme, diglyme and the like; aromatic hydrocarbons such as benzene, toluene, xylene and the like; aliphatic hydrocarbons such as n-hexane, heptane, cyclohexane and the like; amines such as pyridine, N,N-dimethylaniline and the like; and aprotic polar solvents such as N,N-dimethylformamide, dimethyl sulfoxide, hexamethylphosphoric triamide and the like can be exemplified. The reaction may be carried out generally at 0° to 200° C., preferably at room temperature to about 150° C., and the reaction is generally completed in about 0.5 to 10 hours. The ratio of the amount of a compound of the general formula (13) to the amount of a compound of the general formula (12) may generally be at least an equimolar quantity, preferably an equimolar to 1.5 times the molar quantities of the former to the latter.

The reduction of a compound of the general formula (14) can be carried out under conditions similar to those employed in the reduction of a compound of the general formula (11) shown in the above-mentioned Reaction process formula-4.

Compounds of the general formulas (4a) and (4b) can be converted into a compound of the general formula (15)

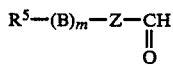

[wherein Z is a group of the formula

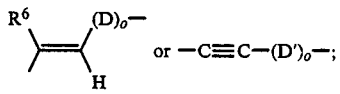

$R^5$, $R^6$, B, m, o and D' are the same as defined above], by oxidizing said compound in the presence of a suitable oxidizing agent.

Some of compounds of the general formula (15) are the starting materials compound of the general formula (9) used in the above-mentioned Reaction process formula-4, therefore, various objective compounds of the general formula (4) can be obtained by carrying out the reactions in the Reaction process formulas-4 and -5 and the above-mentioned oxidation in series. As to the oxidizing agent used in the above-mentioned oxidation, chromium compounds such as potassium chromate, potassium bichromate, chromium trioxide, pyridinium chlorochromate, anhydrous chromium trioxide-pyridine complex and the like; manganese compounds such as a manganese dioxide, potassium permanganate and the like; lead tetraacetate; periodic acid; dimethyl sulfoxide; amine oxides such as dimethylamine oxide; pyridine-nitroso compounds such as pyridine-p-nitroso-N,N-dimethylaniline and the like can be exemplified. As to the solvent used in this reaction, aromatic hydrocarbons such as benzene, toluene, xylene and the like; halogenated hydrocarbons such as methylene chloride, chloroform, carbon tetrachloride and the like; ethers such as diethyl ether, dioxane, tetrahydrofuran and the like; aliphatic hydrocarbons such as hexane, pentane, cyclohexane and the like; ketones such as acetone, methyl ethyl ketone and the like; lower alcohols such as methanol, ethanol, isopropanol and the like; water; acetic acid, dimethyl sulfoxide and the like can be exemplified. The reaction may be carried out generally at 0° to 200° C., preferably at 0° to about 150° C., and is completed generally in 0.5 to 15 hours.

Reaction process formula-6

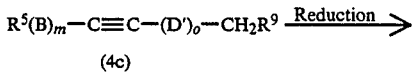

(4c)

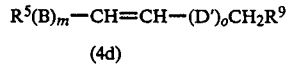

(4d)

[wherein $R^5$, B, D' and m and o are the same as defined above; and $R^9$ is a hydroxyl group or a lower alkanoyl group].

The reduction of a compound of the general formula (4c) can be carried out by a method similar to that known in the art. Thus, a catalytic reduction by using a catalyst such as palladium black, palladium carbon, platinum oxide, platinum black, Raney nickel, Lindlar catalyst and the like, and reduction by using sodium boron hydride, lithium aluminum hydride and the like may be employed. In carrying out the catalytic reduction, the reaction may be conducted in a common solvent such as water, methanol, ethanol, isopropanol, acetic acid, dioxane, tetrahydrofuran or the like, in the presence of the above-mentioned catalyst, at a normal pressure to 20 atmospheric pressure, preferably at normal pressure to 10 atmospheric pressure of hydrogen gas, and generally at −30° C. to 100° C., preferably at 0° C. to 50° C. The amount of the catalyst is generally 0.1 to 40% by weight, preferably 1 to 20% by weight to the amount of a compound of the general formula (4c). The reaction time is generally 1 to 12 hours.

In carrying out the reduction by using lithium aluminum hydride as the reducing agent, the reaction may be conducted by using an equimolar to 20 times the molar quantities, preferably 1.5 to 3.5 times the molar quantities of the reducing agent to the molar quantity of a compound of the general formula (4c), in a usual solvent, such as diethyl ether, tetrahydrofuran, dioxane or the like, at a temperature of generally at −30° to 100° C., preferably at 0° C. to 70° C. for 30 minutes to 12 hours. By carrying out said reduction, there can easily be obtained a compound represented by the general formula (4d).

Among compounds of the general formula (4d), those having lower alkanoyl group as $R^9$ can be converted into compounds in which $R^9$ is hydroxyl group by hydrolysis. Said hydrolysis can be carried out under conditions those employed in common hydrolysis of an ester. For example, the hydrolysis is carried out in the presence of an acid or alkali catalyst, in an inert solvent at a temperature condition of 0° to 100° C. in taking about 1 to 5 hours. As to the catalyst used in the hydrolysis, inorganic acid, such as hydrochloric acid, sulfuric acid, aluminum chloride and the like; organic acids such as acetic acid, formic acid and the like; inorganic basic compounds such as sodium hydroxide, sodium carbonate, potassium hydroxide and the like; ammonia; organic basic compounds such as triethylamine and the like can be exemplified. As to the inert solvent used in the hydrolysis, water; alcohols such as methanol, ethanol and the like; carboxylic acids such as acetic acid, propionic acid and the like; ethers such as diethyl ether and the like; amides such as dimethylformamide, acetamide and the like may be exemplified.

Among compounds of the general formula (4c), some of them can be prepared by the following Reaction process formula-7 as follows.

Reaction process formula-7

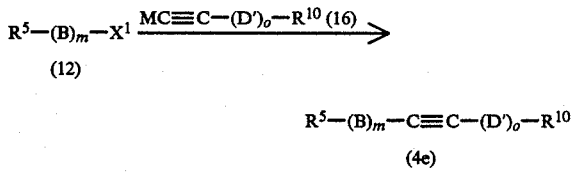

[wherein $R^5$, B, m, $X^1$, M, D' and o are the same as defined above; and $R^{10}$ is a lower alkanoyl group].

The reaction of a compound of the general formula (12) with a compound of the general formula (16) can be carried out by reaction under conditions aimilar to those employed in the reaction of a compound of the general formula (12) with a compound of the general formula (13) in the above-mentioned Reaction process formula-5.

Reaction process formula-8

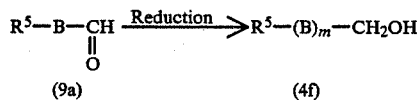

[wherein $R^5$, B and m are the same as defined above].

The reduction of a compound of the general formula (9a) can be carried out under reduction conditions similar to those employed in the reduction of a compound of the general formula (11) in the above-mentioned Reaction process formula-4.

Among compounds represented by the general formula (1), those having a phenyl group for the symbol $R^5$, said phenyl group may have at least one hydroxy group as the substituent, can be prepared by hydrolyzing a compound represented by the general formula (1) in which the symbol $R^5$ is a phenyl group which may have at least one substituent selected from the group consisting of a lower alkoxy group, a tetrahydropyranyloxy group, a lower alkanoyloxy group and a lower alkoxy-lower alkoxy group.

The hydrolysis of a compound represented by the general formula (1) in which the symbol $R^5$ is a phenyl group which may have at least one substituent selected from the group consisting of a lower alkoxy group, a tetrahydropyranyloxy group and a lower alkoxy-lower alkoxy group [hereinafter, this compound is referred to as compound (1a)] is carried out in the absence or presence of a suitable solvent with an acid. As to the solvent used in this hydrolysis, halogenated hydrocarbons such as methylene chloride, chloroform, 1,2-dichloroethane and the like; water; nitrobenzene; aromatic hydrocarbons such as toluene, benzene and the like; saturated hydrocarbon such as hexane, octane and the like; lower alcohols such as methanol, ethanol, isopropanol and the like; ethers such as dioxane, tetrahydrofuran and the like; ketones such as acetone and the like; acetic acid and acetonitrile; and mixed solvents thereof can be exemplified.

As to the acid used in this hydrolysis, mineral acids such as hydrochloric acid, sulfuric acid, hydrobromic acid and the like; p-toluenesulfonic acid, pyridine p-toluenesulfonate; carboxylic acids such as acetic acid, propionic acid and the like; aluminium chloride, tin chlorides, boron fluoride, zinc chloride and the like can be exemplified.

The ratio of the amount of the acid to the amount of a compound of the formula (1a) may be generally 0.01 mole to a large excess amount of the former may be user to the latter.

The reaction temperature may be generally −30° to 200° C., preferably −30° to 100° C., and the reaction is generally completed in 0.5 to about 8 hours.

The hydrolysis of a compound represented by the general formula (1) in which $R^5$ is a phenyl group which may have at least one lower alkoanoyloxy group as the substituent is carried out by a method similar to that employed in a usual hydrolysis of an ester sidely used in the art. For example, the hydrolysis is carried out in the presence of an acid or alkali catalyst, in an inert solvent at 0° to 100° C., for 1 to 5 hours.

As to catalyst used in this hydrolysis, inorganic acids, such as hydrochloric acid, sulfuric acid, aluminium chlorid and the like; organic acids such as acetic acid, formic acid and the like; inorganic basic compounds such as sodium hydroxide, sodium carbonate, potassium hydroxide and the like; organic basic compounds such as ammonia, triethyl amine and the like may be exemplified.

As to the inert solvents, water, alcohols such as methanol, ethanol and the like; carboxylic acids such as acetic acid, propionic acid and the like; ethers such as diethyl ether and the like; amides such as dimethylformamide, acetamide and the like may be exemplified.

Among compounds represented by the general formula (1), those having basic group can be converted into the corresponding salts thereof by treating with a pharmacologically acceptable acid. Examples of said pharmacological acceptable acids including inorganic acids such as sulfuric acid, nitric acid, hydrochloric acid, hydrobromic acid and the like; and organic acids such as oxalic acid, maleic acid, fumaric acid, malic acid, citric acid, benzoic acid and the like.

Compounds of the general formula (1) thus prepared can easily be isolated and purified by methods usually employed in separation, such as precipitation, extraction, recrystallization, column chromatography, preparative layer chromatography and the like.

A compound of the general formula (1) of the present invention contains inevitably its optical isomers.

Compounds represented by the general formula (1) can be administered, either single or together with conventional pharmacologically acceptable carriers, to animals as well as to human beings. No particular restriction is made to the administration unit forms. Thus compounds of the present invention represented by the general formula (1) can be used in any desired administration unit form. Suitable administration unit forms include peroral administration unit forms such as tablets, granules and solutions; and parenteral administration unit forms such as injections.

The dosage of a compound represented by the general formula (1) as the active ingredient to be administered is not subjected to any particular restriction and can be selected from a wide range. For the purpose of attaining the desired pharmacological effects, it is recommended to select a dosage from the range of 0.06 to 10 mg/kg of the body weight/day. It is suggested also to have 1 to 500 mg of the active ingredient in each of the desired administration unit forms.

In the present invention, the desired peroral administration unit forms such as tablets, capsules and solutions can be prepared by conventional methods. For the purpose of shaping the administration unit form into the form of tablets, a ccompound of the present invention is mixed with pharmaceutically acceptable excipients such as gelatin, starch, lactose, magnesium stearate, talcum powder and gum arabic and others. Capsules can be prepared by mixing a compound of the present invention with inert pharmaceutically acceptable fillers or diluents and placing the mixture obtained into rigid gelatin capsules or soft capsules. Sirups or elixiers may be prepared by mixing a compound of the present invention with a sweetening agent such as sucrose; anticeptice such as methyl- or propyl-parabens; colorants; seasoning agents and/or other suitable additives. Parenteral preparations can also be prepared by conventional methods. For example, by dissolving compound of the present invention in a sterilized liquid vehicle. As to the preferable vehicle, water or saline can be used. Liquid preparations having desired transparency, stability and parenteral use adaptability can be prepared by dissolving approximately 1 to 500 mg of the active ingredient in a solution of polyethylene glycol having the molecular weight of 200 to 5,000, which is soluble in both water and organic solvents. Desirably, such liquid preparations may contain a lubricant such as sodium carboxymethyl cellulose, methyl cellulose, polyvinyl pyrrolidone and polyvinyl alcohol. Said liquid preparations may also contain a bactericide and fungicide such as benzyl alcohol, phenol and thiemerosal, and if necessary, an isotonic agent such as sucrose or sodium chloride, a local anesthetic, stabilizer and buffer solutions. Furthermore, for additional assurance of stability, the parenteral compositions may be frozen after filling and dehydrating steps by known lyophilization techniques. The lyophilized powder of the parenteral composition can be returned to a liquid state just before use.

Preparation of Tablets 1,000 Tablets for peroral use, each containing 5 mg of methyl 4-[(1-ethoxy)ethoxy]cinnamyl 1,4-dihydro-2,6-dimethyl-4-(3-nitrophenyl)pyridine-3,5-dicarboxylate are prepared from the following formulation.

| Formulation | Amount (g) |
| --- | --- |
| Methyl 4-[(1-ethoxy)ethoxy]cinnamyl 1,4-dihydro-2,6-dimethyl-4-(3-nitrophenyl)pyridine-3,5-dicarboxylate | 5 |
| Lactose (Japanese Pharmacopoeia official drug grade) | 50 |
| Corn starch (Japanes Pharmacopoeia official drug grade) | 25 |
| Crystalline cellulose (Japanese Pharmacopoeia official drug grade) | 25 |
| Methyl cellulose (Japanese Pharamcopoeia official drug grade) | 1.5 |
| Magnesium stearate (Japanese Pharmacopoeia official drug grade) | 1 |

Methyl 4-[(1-ethoxy)ethoxy]cinnamyl 1,4-dihydro-2,6-dimethyl-4-(3-nitrophenyl)pyridine-3,5-dicarboxylate, lactose, corn starch and crystalline cellulose are mixed well, and the mixture is granulated with 5%-methyl cellulose aqueous solution, then the granules are passed through a 200 mesh sieve and then dried carefully. The dried granules are passed through a 200 mesh sieve and mixed with magnesium stearate, then pressed into the form of tablets.

Preparation of capsules 1,000 Capsules of two-piece rigid gelatin capsules for peroral use, each containing 10 mg of methyl 4-[(1-ethoxy)ethoxy]cinnamyl 1,4-dihydro-2,6-dimethyl-4-(3-nitrophenyl)pyridine-3,5-dicarboxylate are prepared by using the following formulation.

| Formulation | Amount (g) |
| --- | --- |
| Methyl 4-[(1-ethoxy)ethoxy]cinnamyl 1,4-dihydro-2,6-dimethyl-4-(3-nitrophenyl)pyridine-3,5-dicarboxylate | 10 |
| Lactose (Japanese Pharmacopoela official drug grade) | 80 |
| Starch (Japanese Pharmacopoeia official drug grade) | 30 |
| Talcum powder (Japanese Pharmacopoeia official drug grade) | 5 |
| Magnesium stearate (Japanese Pharmacopoeia official drug grade) | 1 |

The above-mentioned ingredients are finely ground, then mixed sufficiently to a uniform mixture and filled into gelatin capsules of a size having desired size for peroral administration.

Preparation of injection solution

A sterile aqueous solution suitable for parenteral use is prepared from the following formulation.

| Formulation | Amount (g) |
| --- | --- |
| Methyl 4-[(1-ethoxy)ethoxy]cinnamyl 1,4-dihydro-2,6-dimethyl-4-(3-nitrophenyl)pyridine-3,5-dicarbosylate | 1 |
| Polyethylene glycol (M. W. = 4,000 (Japanese Pharmacopoeia official drug grade) | 0.9 |
| Sodium chloride (Japanese Pharmacopoeia official drug grade) | 0.9 |
| Polyoxyethylene sorbitan monooleate (Japanese Pharmacopoeia official drug grade) | 0.4 |
| Sodium metabisulfite | 0.1 |
| Methyl p-hydroxybenzoate (Japanese Pharmacopoeia official drug grade) | 0.18 |
| Propyl p-hydroxybenzoate (Japanese Pharmacopoeia official drug grade) | 0.02 |
| Distilled water for injection | 100 (ml) |

The above-mentioned methyl p-hydroxybenzoate, propyl p-hydroxybenzoate, sodium metabisulfite and sodium chloride are dissolved in about a half volume of distilled water at 80° C. under stirring condition. The solution obtained is cooled to 40° C., then methyl 4-[(1-ethoxy)ethoxy]cinnamyl 1,4-dihydro-2,6-dimethyl-4-(3-nitrophenyl)pyridine-3,5-dicarboxylate, polyethylene glycol and polyoxyethylene sorbitan monooleate are dissolved in the solution. Thus obtained solution is further mixed with the distilled water for injection so as to make it into the final volume, then sterilized by sterile filtration with a suitable filter paper.

The present invention will be illustrated more specifically by way of the following examples, in which the preparations of the compounds to be used for the starting materials will be shown in Reference Examples and the preparations of the objective compounds will be shown in Examples. The present invention, however is not restricted to these examples.

Reference Example 1

To 20 g of p-hydroxybenzaldehyde and 32.5 g of monoethyl malonate were added 6 ml of pyridine and 0.2 ml of piperidine, then the mixture thus obtained was heated at 100° to 110° C. for 10 hours under stirring. The reaction mixture was then cooled, extracted with chloroform, and the chloroform layer was washed with an aqueous solution saturated with potassium hydrogen sulfite and water in this order, the chloroform extract was dried with anhydrous magnesium sulfate. The solvent was removed by evaporation and the residue thus obtained was crystallized from isopropyl ether-n-hexane to yield 25.2 g of ethyl 4-hydroxycinnamate. Light yellow indefinite form crystals. Melting point: 70°-71° C.

Reference Example 2

By using 20 g of 3-hydroxybenzaldehyde and 32.5 g of monoethyl malonate as the starting materials, and by a method similar to that described in Reference Example 1, under reaction conditions similar thereto, there was prepared 25.5 g of ethyl 3-hydroxycinnamate. Melting point: 65°-68° C. (Recrystallized from isopropyl ether)

Reference Example 3

By using 25.8 g of 4-hydroxy-3-chlorobenzaldehyde and 32.5 g of monoethyl malonate as the starting materials, and by a method similar to that described in Reference Example 1, under reaction conditions similar thereto, there was prepared 46 g of ethyl 4-hydroxy-3-chlorocinnamate. Colorless prism-like crystals (recrystallized from methylene chloride). Melting point: 118°-119° C.

Reference Example 4

To 30 ml of anhydrous diethyl ether solution containing 5 g of ethyl 4-hydroxycinnamate was added 7.1 ml of dihydropyran and 50 mg of p-toluenesulfonic acid were added, the mixture was stirred at room temperature for 2 hours. Then the reaction mixture was neutralized with 1%-sodium hydroxude solution, washed with water, and dried with anhydrous sodium sulfate. The solvent was removed by evaporation to yield 6.8 g of ethyl 4-(2-tetrahydropyranyloxy)cinnamate. Colorless indefinite form crystatls. Melting point: 52°-53° C.

Reference Example 5

50 Milliliters of anhydrous diethyl ether solution containing 6.8 g of ethyl 4-(2-tetrahydropyranyloxy)-cinnamate was added dropwise to an anhydrous diethyl ether solution being cooled at −30° C. containing 0.47 g of lithium aluminium hydride. After the dropwise addition was finished, the reaction mixture was stirred for 1 hour at the same temperature, then the temperature of the reaction mixture was gradually elevated up to −10° C., then an aqueous solution saturated with sodium sulfate was gradually added to the reaction mixture, and the precipitates formed in the reaction mixture were removed by filtration. The filtrate was dried with anhydrous sodium sulfate, then concentrated to dryness, the residue thus obtained was treated by means of silica gel column chromatography (eluent: chloroform) to yield 3.2 g of 4-(2-tetrahydropyranyloxy)cinnamyl alcohol in the form of colorless oily substance. Refractive index: $n_D^{22}$ 1.5520.

Reference Example 6

15 Grams of 4-tetrahydropyranyloxy)cinnamyl alcohol and 5.2 g of sodium acetate were suspended in anhydrous methylene chloride, then to this suspension was added in one time 18 g of pyridium chlorochromate under ice-cooled condition. The reaction mixture was stirred for 1 hour at the same temperature, then the temperature was elevated to room temperature, and the reaction mixture was stirred for additional 1 hour. 100 Milliliters of diethyl ether was added to the reaction mixture, the whole mixture was filtered with Celite (a trademark for diatomaceous product manufactured by and sold from Johns-Manville Products Corp., Celite Division, New York, N.Y., U. S. A.), the filtrate was concentrated and the residue thus obtained was treated by silica gel column chromatography. Recrystallization from diethyl ether to yield 3.5 g of 4-(2-tetrahydropyranyloxy)-cinnamyl aldehyde in the form of colorless needle-like crystals. Melting point: 65°-67° C.

Reference Example 7

5.6 Grams of triethyl phosphonoacetate was added dropwise under stirring condition at room temperature to a tetrahydrofuran solution containing 1.06 g of 60%-sodium hydride, then the reaction mixture was further stirred at 40° C. for 1 hour. The reaction mixture was cooled to room temperature, then a tetrahydrofuran solution containing 5.6 g of 4-(2-tetrahydropyranyloxy)-cinnamyl aldehyde was added thereto, and stirred at a room temperature for 2 hours, then the reaction mixture was poured into 100 ml of water. The whole mixture was extracted with diethyl ether, and the ether layer was washed with water, and an aqueous solution saturated with sodium chloride in this order, then dried with anhydrous sodium sulfate. Recrystallization from isopropyl ether to yield 3.8 g of ethyl 5-[4-(2-tetrahydropyranyloxy)phenyl]-2(E),4(E)-pentadienoate in the form of colorless needle-like crystals. Melting point: 66°–67.5°.

Reference Example 8

To 30 ml of anhydrous benzene solution containing 3.6 g of ethyl 5-[4-(2-tetrahydropyranyloxy)phenyl]-2(E),4(E)-pentadienoate was added dropwise 15 ml of diisobutyl aluminium hydride (25% by weight/by volume) under water-cooled condition and the reaction mixture was stirred at a room temperature for 2 hours. The reaction mixture was then poured into an aqueous solution saturated with ammonium chloride and stirred at a room temperature for 2 hours. The insoluble matters were collected by filtration with Celite, and the insoluble matters collected were washed with diethyl ether. The organic layer was washed with water and dried with anhydrous sodium sulfate, then concentrated to obtain the residue. The residue was recrystallized from chloroform-n-hexane to yeild 2.8 g of 5-[4-(2-tetrahydropyranyloxy)phenyl]-2(E),4(E)-pentadienol in the form of colorless needle-like crystals. Melting point: 54°–58° C.

REFERENCE EXAMPLE 9

25 Grams of p-hydroxyacetophenone, 50 ml of dihydropyrane and 0.25 g of p-toluenesulfonic acid were stirred at room temperature for 2 hours in anhydrous diethyl ether. Then the reaction mixture was neutralized with 1N-sodium hydroxide and washed with water and an aqueous solution saturated with sodium chloride in this order, then dried with anhydrous sodium sulfate. The product was concentrated to yield 34 g of 4-(2-tetrahydropyranyloxy)acetophenone. Colorless prism-like crystals. Melting point: 79°–83° C.

REFERENCE EXAMPLE 10

45.8 Grams of triethyl phosphonoacetate and an anhydrous tetrahydrofuran solution containing 8.7 g of 60%-sodium hydride were stirred at 40° C. for 1 hour, the reaction mixture was cooled and 30 g of 4-(2-tetrahydropyranyloxy)acetophenone was added to the reaction mixture. The whole reaction mixture was refluxed for 4 hours, then the solvent was removed by evaporation, the residue thus obtained was extracted with diethyl ether and washed with water, than dried. The extract was concentrated and the residue thus obtained was treated by means of silica gel column chromatography to yield 27.5 g of ethyl 3-methyl-p-(2-tetrahydropyranyloxy)cinnamate in the form of light yellow oily substance.

$^1$H-NMR (90 MHz, CDCl$_3$) δ: 1.29 (3H, t, J=6 Hz), 1.4–2.1 (6H, m), 2.49 (3H, d, J=1 Hz), 3.3–3.9 (2H, m), 4.10 (2H, q, J=6 Hz), 5.3–5.45 (1H, m), 6.03 (1H, d, J=6 Hz), 6.9–7.4 (4H, m)

REFERENCE EXAMPLE 11

To a tetrahydrohydrofuran solution containing 27.5 g of ethyl 3-methyl-p-(2-tetrahydropyranyloxy)cinnamate was added dropwise 118 ml of diisobutyl aluminium hydride (25% by weight/volume) at a room temperature. 2 Hours after the dropwise addition, the reaction mixture was poured into an ice-cooled ammonium chloride aqueous solutoin, and the insoluble matters were removed by filtration. The filtrate was washed with water then dried with anhydrous sodium sulfate and concentrated. The residue thus obtained was purified by means of silica gel column chromatography to yield 12.7 g of 3-methyl-p-(2-tetrahydropyranyloxy)cinnamyl alcohol in the form of colorless oily substance.

$^1$H-NMR (90 MHz, CDCl$_3$) δ: 1.5–2.0 (6H, m), 2.0 (3H, s), 3.3–4.0 (2H, m), 4.1–4.3 (3H, m), 5.26–5.4 (1H, m), 5.81 (1H, t, J=6 Hz), 6.8–7.5 (4H, m).

REFERENCE EXAMPLE 12

10 Grams of p-iodophenol, 8 ml of dihydropyrane and a catalytic amount of p-toluenesulfonic acid was dissolved in 30 ml of anhydrous diethyl ether, and the mixture was stirred at room temperature for 2 hours. The reaction mixture was washed with water, dried then the solvent was removed by evaporation to yield 12.4 g of 4-(2-tetrahydropyranyloxy)-1-iodobenzene in the form of yellow oily substance. Boiling point: 84°–87° C. (at 25 mm Hg).

REFERENCE EXAMPLE 13

6.25 Grams of triethyl phosphonocrotonate was added dropwise to a tetrahydrofuran solution containing 1.06 g of 60%-sodium hydride at a room temperature, the reaction mixture was stirred at 40° C. for 1 hour. The temperature of the reaction mixture was cooled to room temperature, then a tetrahydrofuran solution containing 5.0 g of p-(2-tetrahydropyranyloxy)benzaldehyde was added to the reaction mixture, and stirred at room temperature for 2 hours, then the reaction mixture was poured into 100 ml of water. The whole mixture was extracted with diethyl ether, and the diethyl ether extract was washed with water and an aqueous solution saturated with sodium chloride in this order, then dried with anhydrous sodium sulfate. The solvent was removed by evaporation, the residue thus obtained was purified by measns of silica gel column chromatography (eluent: hexane-chloroform), next recrystallized from diisopropyl ether to yield 4.01 g of ethyl 5-[4-(2-tetrahydropyranyloxyphenyl)]-2(E),4(E)-pentadienoate. Colorless needle-like crsytals. Melting point: 66°–67.5° C.

REFERENCE EXAMPLE 14

20 Grams of p-tetrahydropyranyloxyiodobenzene and 70 ml of anhydrous pyridine containing 11.3 g of copper (I) 3-acetyloxy-1-propyn-1-ide were refluxed for 6 hours under an atmosphere of argon gas. After the reaction was completed the reaction mixture was poured into water and the whole mixture was extracted with chloroform. The chloroform layer was washed with water, dried and the solvent was removed by evaporation. The residue thus obtained was purified by means of a silica gel column chromatography (eluent: chlorofrom:n-hexane=1:1) to yield 8 g of 4-[4-(2-tetrahydropyranyloxy)phenyl]-3-butynyl acetate in the form of colorless oily substance.

$^1$H-NMR (60 MHz, CDCl$_3$) δ: 6.98 (2H, d, J=8 Hz), 6.63 (2H, d, J=8 Hz), 6.15 (1H, m), 4.05 (2H, t, J=6 Hz), 3.3–3.7 (2H, m), 2.58 (2H, t, J=6 Hz), 1.97 (3H, s), 1.5–1.9 (6H, m).

REFERENCE EXAMPLE 15

To an anhydrous tetrahydrofuran solution containing 2.4 g of 4-[4-(2-tetrahydropyranyloxy)phenyl]-3-butynyl acetate was added 1 g of lithium aluminium hydride and the mixture was refluxed for 12 hours. After the reaction was completed, an aqueous solution saturated with sodium sulfate was slowly added to the reaction mixture, and the precipitation formed were removed by filtration, then the filtrate was dried with anhydrous sodium sulfate, and concentrated to dryness. The residue thus obtained was purified by means of a silica gel column chromatography to yield 2 g of 4-[(2-tetrahydropyranyloxy)phenyl]-3(E)-butenyl alcohol as in the form of colorless oily substance.

$^1$H-NMR (90 MHz, CDCl$_3$) δ: 1.5–2.1 (6H, m), 2.43 (2H, q, J=6 Hz), 3.4–4.0 (5H, m), 5.37 (1H, m), 6.03 (1H, d, t, J=16 Hz, 6 Hz), 6.40 (1H, d, J=16 Hz), 6.97 (2H, d, J=9 Hz), 7.25 (2H, d, J=9 Hz).

REFERENCE EXAMPLE 16

10 Grams of 4-[(1-ethoxy)ethoxy]cinnamyl acetoacetate was dissolved in 20 ml of toluene, then 2 g of ammonia gas was passed through this solution at about 80° C. with stirring condition. The water formed during the reaction was removed by azeotropic distillation with toluene. 2 Hours after the azeotropic distillation, the toluene was removed by distillation under reduced pressure to yield 10 g of 4-[(1-ethoxy)ethoxy]cinnamyl 3-aminocrotonate as in the form of an oily substance.

NMR (CDCl$_3$) δ: 1.18 (3H, t, J=7.5 Hz), 1.47 (3H, d, J=6 Hz), 1.90 (3H, s), 3.35–3.85 (2H, m), 4.55 (1H, s), 4.68 (2H, d, J=6 Hz), 5.35 (1H, q, J=6 Hz), 6.15 (1H, dt, J=6 Hz, 15.5 Hz), 6.57 (1H, d, J=15.5 Hz), 6.90 (2H, d, J=8.4 Hz), 7.30 (2H, d, J=8 Hz)

IR (film) ν: 3460, 3350, 1610 cm$^{-1}$ Mass spectrospectrometry (M/e) M+ 305.

REFERENCE EXAMPLE 17

Into 5.0 ml of tetrahydrofuran solution containing 1 g of 4-hydroxycinnamyl aldehyde was added 0.5 g of ethyl vinyl ether and 10 ml of p-toluenesulfonic acid and the mixture was allowed to stand at room temperature for 1 hour. Then 3 ml of an aqueous solution containing 0.3 g of sodium boron hydride was added thereto and the whole reaction mixture was allowed to stand at room temperature for 30 minutes. Next the reaction was completed, the reaction mixture was extracted with n-hexane, and the extract was dried with anhydrous magnesium sulfate, then the solvent was removed by evaporation to obtain 1.3 g of 4-[(1-ethoxy)ethoxy]cinnamyl alcohol as in the form of an oily substance.

REFERENCE EXAMPLE 18

36 Milliliters of dichloromethane was added to 12 g of 4-[(1-ethoxy)ethoxy]cinnamyl alcohol, then 60 mg of anhydrous sodium acetate was added thereto. Under refluxing condition, 5 g of diketene was added dropwise to the reaction mixture, and 2 hours later, 0.42 g diketene was further added thereto, the whole reaction mixture was refluxed for 1.5 hours. After the reaction was completed, the dichloromethane was removed by evaporation under reduced pressure, and the residue thus obtained was stirred for 30 minutes with 27 ml of hexane and 1.2 g of activated carbon. The activated carbon was removed by filtration, and the filtrate was concentrated to obtain 15 g of 4-[(1-ethoxy)ethoxy]cinnamyl acetoacetate as in the form of an oily substance.

NMR (CDCl$_3$) δ: 1.15 (3H, t, J=7 Hz), 1.44 (3H, d, J=5.4 Hz), 2.20 (3H, s), 3.31–3.95 (2H, m), 3.45 (2H, s), 4.71 (2H, d, J=6 Hz), 5.35 (1H, q, J=5.2 Hz), 6.10 (1H, dt, J=6.1 Hz, 15.3 Hz), 6.59 (1H, d, J=15.3 Hz), 6.91 (2H, d, J=9 Hz), 7.29 (2H, d, J=9 Hz).

IR (film) ν: 1650, 1730 cm$^{-1}$.

REFERENCE EXAMPLE 19

Into 750 ml of methanol solution containing 151 g of m-nitrobenzaldehyde were added 116 g of methyl acetoacetate and 24.1 g of o-anisidine, then the mixture was allowed to stand at room temperature for 19 hours. The crystals precipitated were collected by filtration, and recrystallized from acetone to obtain 213 g of m-nitrobenzylidene acetoacetate. Melting point: 157°–158° C.

REFERENCE EXAMPLE 20

A solution consisting of 18.6 g of 5-acetyl-2,2-dimethyl-1,8-dioxane-4,6-dione, 22.2 g of 4-(1-ethoxyethoxy)-cinnamyl alcohol and 50 ml of tetrahydrofuran was refluxed for 6 hours. After the reaction was completed, the solvent was removed by evaporation, the residue thus obtained was purified by means of a silica gel column chromatography (eluent: ethyl acetate:n-hexane=1:4) to obtain 5.8 g of 4-[(1-ethoxy)ethoxy]cinnamyl acetoacetate as in the form of an oily substance.

NMR (CDCl$_3$) δ: 1.15 (3H, t, J=7 Hz), 1.44 (3H, d, J=5.4 Hz), 2.20 (3H, s), 3.31–3.95 (2H, m), 3.45 (2H, s), 4.71 (2H, d, J=6 Hz), 5.35 (1H, q, J=5.2 Hz), 6.10 (1H, dt, J=6.1 Hz, 15.3 Hz), 6.59 (1H, d, J=15.3 Hz), 6.91 (2H, d, J=9 Hz), 7.29 (2H, d, J=9 Hz)

IR (film) ν: 1650, 1730 cm$^{-1}$.

REFERENCE EXAMPLE 21

3.0 Grams of m-nitrobenzaldehyde, 2.3 g of methyl acetoacetate and 0.4 g of m-toluidine were dissolved in 15 ml of methanol, and the resulting solution was allowed to stand at 40° C. for 4 hours to let the reaction was completed. The crystals being precipitated in the reaction solution were collected by filtration, and then were washed with methanol. Recrystallized from acetone to obtain 4.1 g of m-nitrobenzylidene acetate. Melting point: 157°–158° C.

REFERENCE EXAMPLES 22–25

By a method under conditions similar to those employed in Reference Example 21, except that each of the following catalyst was used in place of m-toluidine, there were obtained m-nitrobenzylidene acetate in the yield as shown in below.

| Reference Example No. | Catalyst | Amount of catalyst used | Yield of m-nitrobenzylidene acetate obtained |
|---|---|---|---|
| 22 | p-Chloroaniline | 0.5 g | 3.9 g |
| 23 | Aniline | 0.3 g | 3.9 g |
| 24 | p-Toluidine | 0.4 g | 2.7 g |
| 25 | o-Phenetidine | 0.5 g | 4.3 g |

EXAMPLE 1

A mixture of 3.3 g of 4-[(1-ethoxy)ethoxy)cinnamyl 3-aminocrotonate, 2.6 g of m-nitrobenzylidene acetoacetate and 26 ml of isopropanol was refluxed under a nigrogen gas stream with stirring for 3 hours. After the completion of the reaction, the solvent was removed by evaporation under reduced pressure to yield 5.9 g of methyl 4-[(1-ethoxy)ethoxy]cinnamyl 1,4-dihydro-2,6-dimethyl-4-(3-nitrophenyl)pyridine-3,5-dicarboxylate.

IR (KBr): 3370, 1680, 1650, 1610 cm$^{-1}$,

NMR (CDCl$_3$) δ: 1.17 (3H, t, J=7 Hz), 1.47 (3H, d, J=5.5 Hz), 2.34 (6H, s), 3.35–3.95 (2H, m), 3.60 (3H, s), 4.65 (2H, d, J=6 Hz), 5.10 (1H, s), 5.35 (1H, q, J=5.5 Hz), 6.05 (1H, dt, J=6 Hz, 15.5 Hz), 6.46 (1H, d, J=15.5 Hz), 6.89 (2H, d, J=9 Hz), 7.18–8.09 (6H, m).

EXAMPLES 2–28

By a method similar to that described in Example 1, by using a suitable starting material, there were prepared compounds shown in Table 1 as follows.

TABLE 1

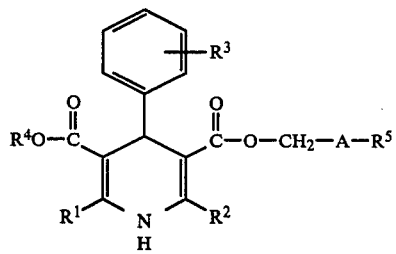

| Example No. | R$^1$ | R$^2$ | R$^3$ | R$^4$ | —CH$_2$—A—R$^5$ | Melting point (°C.) (Recrystallization solvent) | Crystal form |
|---|---|---|---|---|---|---|---|
| 2 | CH$_3$ | CH$_3$ | 3-NO$_2$ | CH$_3$ | -CH$_2$-CH=CH-C$_6$H$_4$-OH (trans, para) | 137.5–139 (Diethyl ether-benzene) IR (KBr): 1600, 1680, 1700 cm$^{-1}$ | Yellow powdery crystals |
| 3 | CH$_3$ | CH$_3$ | 3-NO$_2$ | CH$_3$ | -CH$_2$-CH=CH-C$_6$H$_4$-OH (meta) | 60–63 (Diethyl ether-n-hexane) | Light yellow powdery crystals |
| 4 | CH$_3$ | CH$_3$ | 3-NO$_2$ | CH$_3$ | -CH$_2$-CH=CH-C$_6$H$_4$-OH (ortho) | 75–105 (Diethyl ether-n-hexane) | Light yellow indefinite form crystals |
| 5 | CH$_3$ | CH$_3$ | 3-NO$_2$ | CH$_3$ | -CH$_2$-C(CH$_3$)=CH-C$_6$H$_4$-OH (para) | 181–182 (Methanol) | Yellow powdery crystals |
| 6 | CH$_3$ | CH$_3$ | 3-NO$_2$ | CH$_3$ | -CH$_2$C≡C-C$_6$H$_4$-OH | 173–176 (Tetrahydrofuran-n-hexane) | Yellow prism-like crystals |

TABLE 1-continued

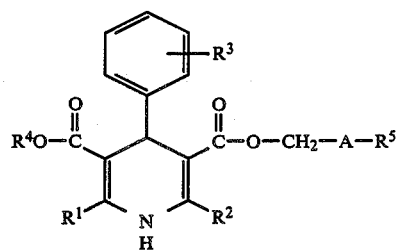

| Example No. | $R^1$ | $R^2$ | $R^3$ | $R^4$ | —CH₂—A—R⁵ | Melting point (°C.) (Recrystallization solvent) | Crystal form |
|---|---|---|---|---|---|---|---|
| 7 | CH₃ | CH₃ | 3-NO₂ | CH₃ | -CH₂-CH=CH-C₆H₄-OH (with vinyl H's shown) | 170–171 (Methanol) | Light yellow powdery crystals |
| 8 | CH₃ | CH₃ | 2-NO₂ | CH₃ | -CH₂-CH=CH-C₆H₄-OH | 90–95 (Tetrahydrofuran-n-hexane) | Light yellow indefinite form crystals |
| 9 | CH₃ | CH₃ | 2-CF₃ | CH₃ | -CH₂-CH=CH-C₆H₄-OH | 164–165 (Methanol-diethyl ether) | Light yellow powdery crystals |
| 10 | CH₃ | CH₃ | 3-NO₂ | CH₃ | -CH₂-CH=CH-C₆H₃(OH)(OCH₃) | 146–153 (Isopropanol) | Yellow powdery crystals |
| 11 | CH₃ | CH₃ | 3-NO₂ | CH | -CH₂CH₂-CH=CH-C₆H₄-SCH₃ | 165–170 (Ethyl acetate-n-hexane) | Light yellow indefinite form crystals |

TABLE 1-continued

Structure: 1,4-dihydropyridine with R³ on phenyl, R⁴O-C(=O)- and -C(=O)-O-CH₂-A-R⁵ at 3,5-positions, R¹ and R² at 2,6-positions, NH.

| Example No. | R¹ | R² | R³ | R⁴ | —CH₂—A—R⁵ | Melting point (°C.) (Recrystallization solvent) | Crystal form |
|---|---|---|---|---|---|---|---|
| 12 | $CH_3$ | $CH_3$ | 2-$NO_2$ | $CH_3$ | -CH₂CH₂-CH=CH-(4-SCH₃-phenyl) (cis) | 145–150 (Ethyl acetate-n-hexane) | Yellow indefinite form crystals |
| 13 | $CH_3$ | $CH_3$ | 3-$NO_2$ | $CH_3$ | -CH₂-CH=CH-(3-Cl-4-OH-phenyl) (cis) | 68–70 (Diethyl ether-n-hexane) | Light yellow powdery crystals |
| 14 | $CH_3$ | $CH_3$ | 3-$NO_2$ | $CH_3$ | -CH₂-CH=CH-(4-OC(=O)CH₃-phenyl) (cis) | NMR¹ | Light yellow indefinite form crystals |
| 15 | $CH_3$ | $CH_3$ | 3-$NO_2$ | $CH_3$ | -CH₂-CH=CH-(4-OTHP*-phenyl) (cis) | NMR² | Light yellow indefinite form crystals |
| 16 | $CH_3$ | $CH_3$ | 3-$NO_2$ | $CH_3$ | -CH₂-CH=CH-(3-OCH₂OCH₃-phenyl) (cis) | NMR³ | Light yellow indefinite form crystals |
| 17 | $CH_3$ | $CH_3$ | 3-$NO_2$ | $CH_3$ | -CH₂-CH=CH-(4-OTHP*-phenyl) (cis) | NMR⁴ | Light yellow indefinite form crystals |

TABLE 1-continued

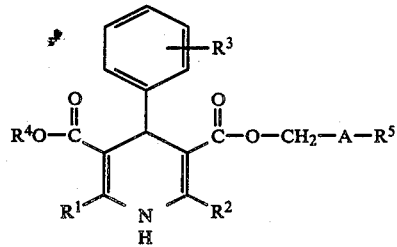

| Example No. | $R^1$ | $R^2$ | $R^3$ | $R^4$ | —CH₂—A—R⁵ | Melting point (°C.) (Recrystallization solvent) | Crystal form |
|---|---|---|---|---|---|---|---|
| 18 | $CH_3$ | $CH_3$ | 3-$NO_2$ | $CH_3$ | —CH₂C≡C—⟨C₆H₄⟩—OTHP* | NMR[5] | Light yellow indefinite form crystals |
| 19 | $CH_3$ | $CH_3$ | 3-$NO_2$ | $CH_3$ | —CH₂—CH=CH—CH=CH—⟨C₆H₄⟩—OTHP* | NMR[6] | Light yellow indefinite form crystals |
| 20 | $CH_3$ | $CH_3$ | 2-$NO_2$ | $CH_3$ | —CH₂—CH=CH—⟨C₆H₄⟩—OTHP* | NMR[7] | Yellow indefinite form crystals |
| 21 | $CH_2$ | $CH_3$ | 2-$CF_3$ | $CH_3$ | —CH₂—CH=CH—⟨C₆H₄⟩—OTHP* | NMR[8] | Light yellow indefinite form crystals |
| 22 | $CH_3$ | $CH_3$ | 3-$NO_2$ | $CH_3$ | —CH₂—CH=CH—⟨C₆H₃(OCH₃)⟩—OTHP* | NMR[9] | Light yellow indefinite form crystals |
| 23 | $CH_3$ | $CH_3$ | 3-$NO_2$ | $CH_3$ | —CH₂—CH=CH—⟨C₆H₃(Cl)⟩—OCH₂OC₂H₅ | NMR[10] | Light yellow indefinite form crystals |

TABLE 1-continued

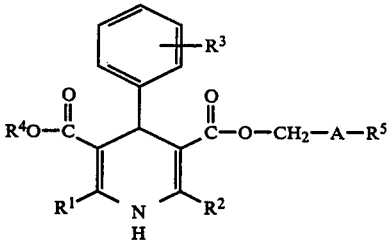

| Example No. | R¹ | R² | R³ | R⁴ | —CH₂—A—R⁵ | Melting point (°C.) (Recrystallization solvent) | Crystal form |
|---|---|---|---|---|---|---|---|
| 24 | CH₃ | CH₃ | 3-NO₂ | CH₃ | 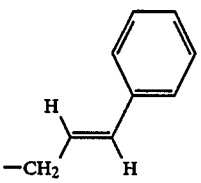 | 120.5–121.5 (Tetrahydrofuran-n-hexane) IR (KBr): 3320, 3260, 3100, 2960, 1700, 1640, 750, 710, 690 cm⁻¹ | Yellow powdery crystals |
| 25 | CH₃ | CH₃ | 3-NO₂ | CH₃ | 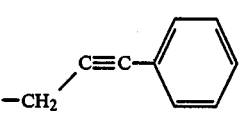 | 122–124 (Tetrahydrofuran-n-hexane) | Light yellow powdery crystals |
| 26 | CH₃ | CH₃ | 3-NO₂ | CH₃ | 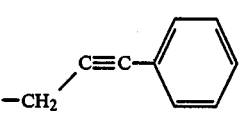 | 92–95 (Chloroform-n-hexane) | Light yellow powdery crystals |
| 27 | CH₃ | CH₃ | 3-NO₂ | CH₃ | 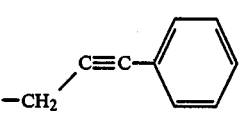 | NMR¹² | Yellow oily substance |
| 28 | CH₃ | CH₃ | 3-NO₂ | CH₃ | 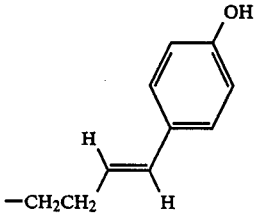 | NMR¹¹ | Light yellow prism-like crystals |

*OTHP: 2-tetrahydropyranyloxy group

NMR¹ (90MHz, CDCl₃):
2.28 (3H, s), 2.35 (6H, s), 3.64 (3H, s), 4.67 (2H, d, J=7Hz), 5.12 (1H, s), 6.06 (1H, broad, s), 6.15 (1H, d, t, Ja=7H, Jb=16Hz), 6.50 (1H, d, J=16Hz), 7.03 (2H, d, J=8Hz), 7.30 (2H, d, J=8Hz), 7.32 (1H, t, J=8Hz), 7.63 (1H, dt, Ja=2Hz, Jb=8Hz), 7.97 (1H, d, t, Ja=2Hz, Jb=8Hz), 8.12 (1H, t, J=2Hz)

NMR² (90MHz, CDCl₃):
1.45–2.10 (6H, m), 2.30 (6H, t), 3.40–4.00 (2H, m), 3.56 (3H, s), 4.63 (2H, d, J=6Hz), 5.10 (1H, s), 5.37 (1H, t, J=3Hz), 6.17 (1H, d, t, Ja=6Hz, Jb=16Hz), 6.45 (1H, d, J=16Hz), 6.65=7.20 (4H, m), 7.30 (1H, t, J=7Hz), 7.62 (1H, d, t, Ja=2Hz, Jb=7Hz), 7.95 (1H, d, t, Ja=2Hz, Jb=7Hz), 8.13 (1H, t, J=2Hz)

NMR³ (90MHz, CDCl₃):
2.30 (3H, s), 2.32 (3H, s), 3.38 (3H, s), 3.53 (3H, s), 4.65 (2H, d, J=7Hz), 5.10 (1H, s), 5.13 (2H, s), 6.20 (1H, dt, Ja=6Hz, Jb=16Hz), 6.47 (1H, s), 6.87 (1H, d, J=16Hz), 6.87–7.48 (5H, m), 7.62 (1H, dt, Ja=2Hz, Jb=7Hz), 7.93 (1H, dt, Ja=2Hz, Jb=8Hz), 8.12 (1H, t, J=2Hz)

NMR⁴ (90MHz, CDCl₃):
1.50–1.95 (6H, m), 1.97 (3H, s), 2.32 (6H, s), 3.34–3.90 (1H, m), 3.53 (3H, s), 4.65 (2H, d, J=7Hz), 5.03 (1H, s), 5.33 (1H, t, J=3Hz), 5.70 (1H, t, J=7Hz), 5.95 (1H, broad, s), 6.97 (2H, d, J=9Hz), 7.23 (2H, d, J=9Hz), 7.28 (1H, t, J=7Hz), 7.58 (1H, d, t, Ja=2Hz, Jb=7Hz), 7.93 (1H, dt, Ja=2Hz, Jb=7Hz), 8.08 (1H, t, J=2Hz).

NMR⁵ (90MHz, CDCl₃):

TABLE 1-continued

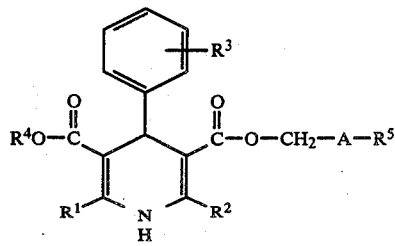

| Example No. | R¹ | R² | R³ | R⁴ | —CH₂—A—R⁵ | Melting point (°C.) (Recrystallization solvent) | Crystal form |
| --- | --- | --- | --- | --- | --- | --- | --- |

1.30–2.0 (6H, m), 2.32 (6H, s), 3.53 (3H, s), 3.3–3.95 (2H, m), 4.79 (2H, s), 5.07 (1H, s), 5.33 (1H, t, J=3Hz), 6.02 (1H, s), 6.93 (2H, d, J=10Hz), 7.28 (2H, d, J=10Hz), 7.27 (1H, t, J=8Hz), 7.66 (1H, d, J=8Hz), 7.93 (1H, d, J=8Hz), 8.10 (1H, s)
NMR⁶ (90MHz, CDCl₃):
1.40–2.10 (6H, m), 2.32 (6H, x), 3.43 (3H, s), 3.20–3.85 (2H, m), 4.43 (2H, d, J=7Hz), 4.95 (1H, s), 5.23 (1H, t, J=3Hz), 5.40–5.80 (1H, m), 5.93–6.53 (3H, m), 6.60 (1H, s), 6.87 (2H, d, J=10Hz), 7.20 (2H, d, J=10Hz), 7.23 (1H, t, J=8Hz), 7.53 (1H, d, t, Ja=2Hz, Jb=8Hz), 7.88 (H, d, t, Ja=2Hz, Jb=8Hz)
NMR⁷ (60MHz, CDCl₃):
1.40–2.0 (6H, m), 2.30 (3H, s), 2.33 (3H, s), 3.20–3.90 (2H, m), 3.60 (3H, s), 4.63 (2H, d, J−6Hz), 5.37 (1H, t, J−3Hz), 5.80 (1H, s), 6.03 (1H, d, t, Ja=6Hz, Jb=16Hz), 6.80 (1H, s), 6.38 (1H, d, J=16Hz), 6.90 (2H, d, J=9Hz), 7.20 (2H, d, J=9Hz), 6.75–7.80 (4H, m)
NMR⁸ (90MHz, CDCl₃):
1.43–2.15 (6H, m), 2.30 (6H, s), 3.38 (3H, s), 3.20–3.80 (2H, m), 4.47 (2H, dd, Ja=3Hz, Jb=7Hz), 5.23 (1H, t, J=3Hz), 5.43 (1H, s), 6.83 (1H, broad, s), 5.94 (1H, dt, Ja=6Hz, Jb=16Hz), 6.23 (1H, d, J=16Hz), 6.87 (2H, d, J=0Hz), 7.13 (2H, d, J=9Hz), 6.75–7.60 (4H, m)
NMR⁹ (90MHz, CDCl₃):
1.5–2.1 (6H, m), 2.28 (3H, s), 3.53 (3H, s), 3.76 (3H, s), 3.4–4.1 (1H, m), 4.57 (2H, d, J=6Hz), 5.27 (1H, t, J=3Hz), 5.99 (1H, dt, Ja=6Hz, Jb=16Hz), 6.07 (1H, s), 6.36 (1H, d, J=16Hz), 6.73 (1H, d, J=7Hz), 6.78 (1H, s), 6.93 (1H, d, J=7Hz), 7.18 (1H, t, J=7Hz), 7.50 (1H, dt, Ja=2Hz, Jb=7Hz), 7.83 (1H, dt, Ja=2Hz, Jb=7Hz), 7.99 (1H, t, J=2Hz)
NMR¹⁰ (60MHz, CDCl₃):
1.24 (3H, t, J=7Hz), 2.37 (3H, s), 3.66 (3H, s), 3.79 (2H, q, J=7Hz), 4.70 (2H, d, J=6Hz), 5.16 (1H, s), 5.30 (2H, s), 5.91 (1H, broad, s), 6.10 (1H, dt, Ja=6Hz, Jb=16Hz), 6.40 (1H, d, J=16Hz), 7.00–7.47 (4H, m), 7.64 (1H, dt, Ja=2Hz, Jb=7Hz), 7.97 (1H, dt, Ja=2Hz, Jb=7Hz), 8.14 (1H, t, J=2Hz)
NMR¹¹ (90MHz, CDCl₃):
1.40–2.10 (6H, m), 2.26 (6H, m), 3.53 (3H, s), 3.40–4.0 (2H, m), 4.58 (2H, d, J=6Hz), 5.03 (1H, s), 5.30 (1H, t, J=3Hz), 5.97 (1H, dt, Ja=6hz, Jb=16Hz), 6.30 (1H, broad, s), 6.37 (1H, d, J=16Hz), 6.88 (2H, d, J=9Hz), 7.14 (2H, d, J=9Hz), 7.20 (1H, t, J=6Hz), 7.50 (1H, dt, Ja=2Hz, Jb=6Hz), 7.82 (1H, dt, Ja=2Hz, Jb=6Hz), 8.00 (1H, t, J=2Hz)
NMR¹² (90MHz, CDCl₃):
1.5–2.1 (6H, m), 2.33 (6H, s), 2.48 (2H, q, J=6Hz), 3.58 (3H, s), 3.5–4.0 (2H, m), 4.15 (2H, t, J=6Hz), 5.09 (1H, s), 5.40 (1H, m), 5.93 (1H, d, t, J=15Hz, 6Hz), 6.30 (1H, s), 6.32 (1H, d, J=15Hz), 6.96 (2H, d, J=9Hz), 7.19 (2H, d, J=9Hz), 7.1–7.3 (1H, m), 7.5=7.7 (1H, d, m, J=6Hz), 7.8–8.0 (1H, d, m, J=6Hz), 8.10 (1H, m)

EXAMPLE 29

22.9 Grams of 4-(1-ethoxyethoxy)cinnamyl methyl 2,6-dimethyl-4-(3-nitrophenyl)-1,4-dihydropyridine was dissolved in 114.5 ml of methylene chloride, and the resulting solution was cooled at 5° C., then 6.9 ml of methanol solution containing 0.41 g of p-toluenesulfonic acid —H₂O was added to the solution in one time. The reaction mixture was stirred for 40 minutes at 5° C. Next 5%-sodium bicarbonate aqueous solution was added to adjust the pH of the organic layer about pH 7–7.5. The aqueous layer was removed, and the organic layer was wahsed with water, an aqueous solution saturated with sodium chloride, then dried with anhydrous magnesium sulfate. Then the organic layer was concentrated at 20°–25° C., and the residue thus obtained was recrystallized from ethanol to obtain 9.8 g of (4-hydroxyphenyl)-2(E)-propenyl methyl 2,6-dimethyl-4-(3-nitrrphenyl)-1,4-dihydropyridine-3,5-dicarboxylate. Melting point: 145.8°–149.4° C.

IR (KBr) ν: 1670 cm⁻¹

In the above example, the residue was recrystallized from diethyl ether in place of ehtnaol to obtain 19.8 g of (4-hydroxyphenyl)-2(E)-propenyl methyl 2,6-dimethyl-4-(3-nitrophenyl)-1,4-dihydropyridine-3,5-dicarboxylate. Melting point: 163°–164° C.

IR (KBr) ν: 1660, 1680 cm⁻¹

EXAMPLE 30

1 Kilogram of cinnamyl 3-aminocrotonate and 1.15 kg of m-nitrobenzilidene acetate were admixed with 4 liters of methanol, then the mixture was refluxed for 10 to 15 hours under stirring condition. After the reaction was completed, 4 liters of methanol was added to the reaction mixture and stirred the cooled. The crystals precipitated from the methanol solution were collected by filtration, then recrystallized from methanol to obtain 1.6 kg of methyl cinnamyl 1,4-dihydro-2,6-dimethyl-4-(3-nitrophenyl)pyridine-3,5-dicarboxylate. Melting point: 143.2°–144.5° C. Yellow powdery substance.

IR (KBr) ν: 3350, 3270, 3100, 3050, 2960 1700, 1660, 750, 740, 700 cm⁻¹

Pharmacological tests

The results of the pharmacological test on dihydropyridine derivatives of the present invention are shown below.

The test compounds used in the tests are as follows.

| Test Compound No. | |
| --- | --- |
| 1. | Methyl 3-(4-hydroxyphenyl)-2(E)-propenyl 1,4-dihydro-2,6-dimethyl-4-(3-nitrophenyl)pyridine-3,5-dicarboxylate |
| 2. | Methyl 3-phenyl-2(E)-propenyl 1,4-dihydro-2,6-dimethyl-4-(3-nitrophenyl)pyridine-3,5- |

| Test Compound No. | |
|---|---|
| | dicarboxylate |
| 3. | Methyl 5-(4-hydroxyphenyl)-2(E),4(E)-pentadienyl 1,4-dihydro-2,6-dimethyl-4-(3-nitrophenyl)-pyridine-3,5-dicarboxylate |
| 4. | Methyl 3-methyl-3-(4-hydroxyphenyl)-2(E)-propenyl 1,4-dihydro-2,6-dimethyl-4-(3-nitrophenyl)pyridine-3,5-dicarboxylate |
| 5. | Methyl 3-phenyl-2-propynyl 1,4-dihydro-2,6-dimethyl-4-(3-nitrophenyl)pyridine-3,5-dicarboxylate |
| 6. | Methyl 3-phenylpropyl 1,4-dihydro-2,6-dimethyl-4-(3-nitrophenyl)pyridine-3,5-dicarboxylate [Reference compound: Japanese Patent Application Kokai (Laid-open) No. 56-36455 (1981)] |
| 7. | Methyl 3-(3-methoxy-4-hydroxyphenyl)-2(E)-propenyl 1,4-dihydro-2,6-dimethyl-4-(3-nitrophenyl)pyridine-3,5-dicarboxylate |
| 8. | Methyl 3-(4-methoxyphenyl-2(E)-propenyl 1,4-dihydro-2,6-dimethyl-4-(3-nitrophenyl)-pyridine-3,5-dihydrocarboxylate |
| 9. | Methyl 3-(3-chloro-4-hydroxyphenyl)-2(E)-propenyl 1,4-dihydro-2,6-dimetyyl-4-(3-nitrophenyl)pyridine-3,5-dicarboxylate |
| 10. | Methyl 3-(4-hydroxyphenyl)-2-propynyl 1,4-dihydro-2,6-dimetyyl-4-(3-nitrophenyl)-pyridine-3,5-dicarboxylate |
| 11. | Methyl 3-(2-hydroxyphenyl)-2(E)-propenyl 1,4-dihydro-2,6-dimethyl-4-(3-nitrophenyl)-pyridine-3,5-dicarboxylate |
| 12. | Methyl 3-(4-hydroxyphenyl)-2(E)-propenyl 1,4-dihydro-2,6-dimethyl-4-(2-trifluoro-methylphenylO)pyridine-3,5-dicarboxylate |
| 13. | Methyl 4-(4-methylthiophenyl)-3(E)-butenyl 1,4-dihydro-2,6-dimethyl-4-(3-nitrophenyl)-pyridine-3,5-dicarboxylate |
| 14. | Methyl 3-(4-acetyloxyphenyl)-2(E)-propenyl 1,4-dihydro-2,6-dimethyl-4-(3-nitrophenyl)-pyridine-3,5-dicarboxylate |
| 15. | Methyl 3-(4-hydroxyphenyl)-2(E)-propenyl 1,4-dihydro-2,6-dimethyl-4-phenylpyridine-3,5-dicarboxylate |
| 16. | Methyl 3-(4-hydroxyphenyl)-2(E)-propenyl 1,4-dihydro-2,6-dimethyl-4-(2-methylphenyl)-pyridine-3,5-dicarboxylate |
| 17. | Methyl 3-(3-hydroxyphenyl)-2(E)-propenyl 1,4-dihydro-2,6-dimethyl-4-(2-nitrophenyl)-pyridine-3,5-dicarboxylate |
| 18. | Methyl 2-(N—methyl-N—benzylamino)ethyl 1,4-dihydro-2,6-dimetyyl-4-(3-nitrophenyl)pyridine-3,5-dicarboxylate [Reference compound known as "Nicardipine"] |

PHARMACOLOGICAL TEST-1

Vasodilative effects of the dihydropyridine derivatives of the present invention were determined by measuring the systolic blood pressures of test animals before and after the administration of test compound.

Systolic blood pressures and heart beat of SHR-rats (spontaneously hypertensive rats) were determined by a "tail cuff method". Thus the test animal was placed in a thermostat chamber (Type: FR-12RS, manufactured by Isuze & Co.) and was warmed at 40° C. for 15 minutes so as to vasodilate the tail arteria, the systolic blood pressures were measured by an electro sphygmomanometer (Type: PE-300, manufactured by Narco-Biosystems, Inc.) and recorded by an ink-writing recorder (Type: RECTIHORIZ 8s, manufactured by San-Ei Instrument & Co.). The experiments were conducted under non-anesthetized and semi-confinement conditions. The test compound was orally administered forcedly by using a sonde for oral administration. The test compound was suspended in 0.15%-gum arabic powder aqueous solution so as to make the quantity of the test compound to 2.5 ml/kg. The test animal was not fasted, and the systolic blood pressures (mm-Hg) were measured before the administration (hereinafter referred to as "PRE") and after the administration (8, 24, 30, 48, 54 and 72 hours after the administration) of the test compound. The data of systolic blood pressure measured before the administration are shown in absolute value of mmHg, and the data measured after the administration are shown in the differences from the absolute values. The results are shown in Table 2 as follows.

TABLE 2

| Test Compound No. | Dosage (mg/kg) p.o. | PRE | Blood pressure (mm-Hg) After the administration (Hours) | | | | | |
|---|---|---|---|---|---|---|---|---|
| | | | 8 | 24 | 30 | 48 | 54 | 72 |
| 1 | 30 | 195.0 | — | −41.0 | −52.0 | −26.5 | −19.8 | −12.5 |
| 2 | 30 | 187.4 | — | −38.6 | −21.2 | −21.0 | −19.2 | — |
| 3 | 30 | 180.8 | — | −31.0 | −30.8 | −15.6 | −12.6 | — |
| 4 | 30 | 184.4 | — | −18.0 | −25.8 | −19.8 | −14.6 | — |
| 5 | 30 | 180.8 | — | −75.4 | −66.8 | −20.8 | −10.6 | −9.6 |
| 6 | 30 | 185.0 | −20.3 | +1.8 | — | — | — | — |

As can be seen the data shown in Table 2, the vasodilative effects of the dihydropyridine derivatives of the present invention can be prolonged for certain length of period as compared with that of the reference compounds.

PHARMACOLOGICAL TEST-2

Calmodulin (calcium-dependent modulator protein) inhibitory activity of each of the test compounds was determined by judging from the difference between IC$_{50}$ (50%-inhibitory concentration) of calmodulin inhibitory activity of the test compound being measured in the presence of calmodulin together with calmodulin-dependent cyclic-AMP phosphodiesterase, and another IC$_{50}$ of calmodulin-dependent cyclic-AMP phosphodiesterase inhibitory activity of the same test compound being measured in the absence of calmodulin. In other words, calmodulin-specific-inhibitory activity of each of the test compounds was determined in case that the test compound shows higher inhibitory activity against calmodulin-dependent cyclic-AMP phosphodiesterase in the presence of calmodulin than another inhibitory activity against calmodulin-dependent cyclic-AMP phosphodiesterase only.

(1) Reagents used in the test (1) Calmodulin: A calmodulin product manufactured by Amano & Co., which was isolated from the brain of bovine, and purified so as to be considered as a single substance with respect to SDS-page (polyacrylamide gel electrophoresis) method.

(2) Calmodulin-dependent cyclic-AMP phosphodiesterase (EC 3.1.4.17): An enzyme substance isolated from the heart of bovine and purified partially by a method of modified version of the disclosure in H. C. Ho, T. S. Teo, et al.: "Biochim. Biophys. Acta", 429, 461 (1976).

(3) 5'-Nucleotidase (EC 3.1.3.5): Grade IV substance (isolated from *Crotalus adamanteus* venom) manufactured by Sigma & Co.

(4) Others: Remainder of the reagents used in the test were those of reagent grade chemicals manufactured by Wako Pure-Chemical Industries, Ltd.

(2) Method for the test

Calmodulin inhibitory activity of each of the test compounds was measured by a method of modified version of the disclosure in T. S. Teo and T. H. Wang: "J. Bio. Chem.", 248, 588 (1973).

(1) Cyclic-AMP-phosphodiesterase: One unit thereof hydrolyzes 1.0 micromole of 3':5'-cyclic-AMP to 5'-AMP per minute at pH 7.5 at 30° C., in the presence of a saturating level of calmodulin.

(2) Calmodulin: One unit thereof stimulates 0.015 activated unit of cyclic-AMP phosphodiesterase to 50% of the maximum activity of the enzyme.

(3) 5'-Nucleotidase: One unit thereof hydrolyzes 1.0 micromole of inorganic phosphorus from adnosine 5'-monophosphate per minute at pH 9.0 at 37° C.

(3) Reactions in the tests (1) Calmodulin-cyclic-AMP phosphodiesterase inhibitory activity:

40 mM of Imidazol, 20 mM of $MgCl_2$, 20 mM of $CaCl_2$, 0.008 8nit of cyclic-AMP phosphodiesterase, 1.0 unit of calmodulin, 0.2 unit of 5'-nucleotidase and 1.0 ml of 10 mM-tris(hydroxymethyl)aminomethane/HCl buffer solution (pH 7.0) containing 0.5 mM of cyclic-AMP were mixed together, and reacted at 30° C. for 30 minutes. Each of the test compounds were dissolved in methanol or N,N-dimethylformamide as the solvent, provided that the quanitty of the solvent was not exceed 2% of the total amount of the mixture. After the reaction was completed, the reaction mixture was ice-cooled, and 0.5 ml each of aqueous solutions of 16.5%-trichloroacetic acid, 1%-thiourea, 3%-ammonium ferrous sulfate were respectively added to the reaction mixture. Further, 0.15 ml of 4.4%-ammonium molibdate solution was added to the mixture and the whole of the mixture was stirred, and was centrifuged at 3,000 r.p.m. for 10 minutes. Then, the centrifuged mixture was allowed to stand at a room temperature for 20 minutes. The $OD_{660\,nm}$ (optical density at 660 nm) was measured.

(2) Cyclic-AMP phosphodiesterase inhibitory activity:

The reaction was conducted by a method similar to that described in (1) as mentioned above, except that 1 mM of EGTA [ethylene glycol-bis(β-aminoethyl ether)-N,N-tetraacetic acid] was used in place of 20 mM of $CaCl_2$. The reaction was conducted for 3 hours. The results are shown in Table 3 as follows.

TABLE 3

| Test Compound No. | Calmodulin-cyclic-AMP phosphodiesterase IC$_{50}$ (μg/ml) | Cyclic-AMP phosphodiesterase IC$_{50}$ (μg/ml) |
| --- | --- | --- |
| 1 | 4.1 | 60 |
| 2 | 2.5 | >100 |
| 3 | 0.85 | >100 |
| 7 | 5.2 | 86 |
| 8 | 2.7 | >100 |
| 9 | 5.3 | >100 |
| 10 | 0.78 | 13 |
| 11 | 1.65 | 12.5 |
| 12 | 6.25 | >100 |

TABLE 3-continued

| Test Compound No. | Calmodulin-cyclic-AMP phosphodiesterase IC$_{50}$ (μg/ml) | Cyclic-AMP phosphodiesterase IC$_{50}$ (μg/ml) |
| --- | --- | --- |
| 13 | 0.062 | 0.23 |
| 14 | 3.0 | 50 |
| 15 | 6.8 | 32 |
| 16 | 5.8 | 58 |
| 17 | 0.9 | 24.6 |
| 18 | 6.25 | 13 |

As can be seen from the data shown in Table 3. the dihydropyridine derivatives of the present invention have specific inhibitory activity against calmodulin as compared with that of indicated by known compound.

What is claimed is:

1. A process for preparing dihydropyridine derivatives and salts and esters thereof represented by the formula:

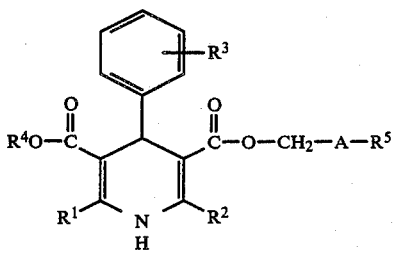

wherein $R^1$, $R^2$ and $R^4$ are each a lower alkyl group; $R^3$ is a nitro group or a lower alkyl group which may have from 1 to 3 halogen atoms as substituents; $R^5$ is a phenyl group which may have from 1 to 3 substituents selected from the group consisting of a lower alkoxy group, a halogen atom, a lower alkylthio group, a hydroxyl group, a lower alkanoyloxy group, a tetrahydropyranyloxy group and a lower alkoxy-lower alkoxy group; and A is an unsaturated straight- or branched-chain hydrocarbon residue, by reacting a compound of the formula

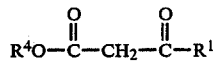

wherein $R^1$ and $R^4$ are the same as defined above, with a compound of the formula,

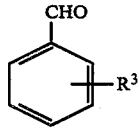

wherein $R^3$ is the same as defined above, in the presence of an aromatic amine selected from the group consisting of, o-anisidine, p-anisidine, m-anisidine, m-toluidine p-toluidine, p-chloroaniline, aniline and o-phenetidine, to obtain a phenyl derivative represented by the formula,

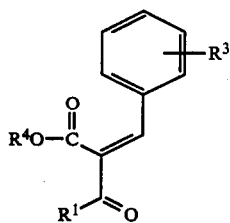
and then reacting the phenyl derivative with an enamine derivative represented by the formula,
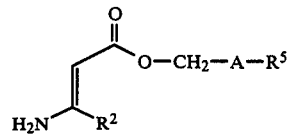
wherein $R^2$ and $R^5$ and A are each of the same as defined above.
2. The process of claim 1, wherein the aromatic amine is selected from the group consisting of m-toluidine, p-toluidine, p-chloroaniline, aniline and o-phenetidine.
* * * * *